(12) United States Patent
Brace et al.

(10) Patent No.: US 11,022,564 B2
(45) Date of Patent: *Jun. 1, 2021

(54) LIGHT DETECTION SYSTEM AND METHOD OF USING SAME

(71) Applicant: 3M INNOVATIVE PROPERTIES COMPANY, St. Paul, MN (US)

(72) Inventors: Thomas J. Brace, Star Prairie, WI (US); Phillip A. Bolea, Grant, MN (US); Giuseppe M. Bommarito, Stillwater, MN (US); Michele A. Waldner, Hudson, WI (US); Stephen R. Alexander, Stillwater, MN (US); Fusu Thao, Cottage Grove, MN (US); Kathleen M. Stenersen, St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/785,849

(22) Filed: Feb. 10, 2020

(65) Prior Publication Data

US 2020/0191727 A1 Jun. 18, 2020

Related U.S. Application Data

(63) Continuation of application No. 15/557,904, filed as application No. PCT/US2016/020548 on Mar. 3, 2016, now Pat. No. 10,613,038.

(Continued)

(51) Int. Cl.
*G01N 21/94* (2006.01)
*C12Q 1/00* (2006.01)
(Continued)

(52) U.S. Cl.
CPC ............ *G01N 21/94* (2013.01); *C12Q 1/008* (2013.01); *C12Q 1/22* (2013.01); *C12Q 1/66* (2013.01);
(Continued)

(58) Field of Classification Search
CPC ............... G01N 21/94; G01N 21/763; G01N 2201/022; G01N 2201/064; G01N 21/76;
(Continued)

(56) References Cited

U.S. PATENT DOCUMENTS 4,755,055 A 7/1988 Johnson et al.
5,086,233 A 2/1992 Stafford et al.
(Continued)

FOREIGN PATENT DOCUMENTS

DE 198 40 055 3/2000
GB 2 223 095 3/1990
(Continued)

OTHER PUBLICATIONS

Brochure entitled "3M™ Clean-Trace™ System—More reliable, ATP tests" from 3M Company; 2007; 2 pgs.

*Primary Examiner* — John R Lee
(74) *Attorney, Agent, or Firm* — Eric E. Silverman

(57) ABSTRACT

Various embodiments of a light detection device and a method of using the device are disclosed. In one or more embodiments, the light detection device can include a housing that extends along a housing axis between top and bottom surfaces. The device can also include a port that is adapted to receive a sample, and a door connected to the housing. The door can include an actuator portion adapted to selectively move the door between a closed position and an open position, and a cover portion connected to the actuator portion and adapted to close the port when the door is in the (Continued)

closed position and open the port when the door is in the open position to allow external access to the port.

19 Claims, 11 Drawing Sheets

Related U.S. Application Data

(60) Provisional application No. 62/132,790, filed on Mar. 13, 2015.

(51) Int. Cl.
| | |
|---|---|
| *C12Q 1/22* | (2006.01) |
| *C12Q 1/66* | (2006.01) |
| *G01J 1/02* | (2006.01) |
| *G01J 1/42* | (2006.01) |
| *G01N 21/76* | (2006.01) |

(52) U.S. Cl.
CPC ........... *G01J 1/0223* (2013.01); *G01J 1/0233* (2013.01); *G01J 1/0271* (2013.01); *G01J 1/42* (2013.01); *G01N 21/763* (2013.01); *C12Q 2304/60* (2013.01); *G01N 2201/021* (2013.01); *G01N 2201/022* (2013.01); *G01N 2201/0221* (2013.01); *G01N 2201/064* (2013.01); *G01N 2201/0646* (2013.01)

(58) Field of Classification Search
CPC ..... G01N 2201/0646; G01N 2201/021; G01N 2201/0221; C12Q 1/008; C12Q 1/22; C12Q 1/66; C12Q 2304/60; C12Q 1/00; G01J 1/42; G01J 1/02; G01J 1/0204; G01J 1/0223; G01J 1/0233; G01J 2001/0257; G01J 1/0271; E05D 3/00; E05D 3/02; E05D 3/022
See application file for complete search history.

(56) References Cited

U.S. PATENT DOCUMENTS

| | | | |
|---|---|---|---|
| 5,827,675 A | 10/1998 | Skiffington et al. | |
| 6,055,050 A | 4/2000 | Skiffington | |
| 6,197,254 B1 | 3/2001 | Silver et al. | |
| 6,653,147 B2 | 11/2003 | DiCesare | |
| 7,981,362 B2 | 7/2011 | Glezer et al. | |
| 8,926,598 B2 | 1/2015 | Mollere et al. | |
| D758,224 S | 6/2016 | Bolea et al. | |
| 9,446,406 B2 | 9/2016 | Gordon et al. | |
| 9,782,114 B2 | 10/2017 | Reynolds et al. | |
| 9,986,212 B2 | 5/2018 | Schneider et al. | |
| 10,422,753 B2 | 9/2019 | Bolea et al. | |
| 10,613,038 B2* | 4/2020 | Brace | G01N 21/94 |
| 2003/0119030 A1 | 6/2003 | Zilber | |
| 2004/0149899 A1 | 8/2004 | Packman et al. | |
| 2004/0220748 A1 | 11/2004 | Feldsine et al. | |
| 2005/0089995 A1 | 4/2005 | Jones | |
| 2006/0166371 A1 | 7/2006 | Testa et al. | |
| 2006/0216196 A1 | 9/2006 | Satoh et al. | |
| 2007/0257202 A1 | 11/2007 | Walker | |
| 2008/0261294 A1 | 10/2008 | Noda et al. | |
| 2010/0068750 A1 | 3/2010 | Pogosjan et al. | |
| 2010/0129840 A1 | 5/2010 | Charm et al. | |
| 2011/0143947 A1 | 6/2011 | Chamberlin et al. | |
| 2012/0135511 A1 | 5/2012 | Battrell et al. | |
| 2012/0329016 A1 | 12/2012 | Bennion et al. | |
| 2013/0172698 A1 | 7/2013 | Reynolds et al. | |
| 2014/0004548 A1 | 1/2014 | Gordon et al. | |
| 2014/0154792 A1 | 6/2014 | Moynihan et al. | |
| 2014/0376762 A1 | 12/2014 | Lipman et al. | |
| 2017/0030841 A1 | 2/2017 | Gordon et al. | |
| 2018/0008178 A1 | 1/2018 | Reynolds et al. | |
| 2018/0058919 A1 | 3/2018 | Thao et al. | |
| 2018/0059031 A1 | 3/2018 | Brace et al. | |
| 2018/0113076 A1* | 4/2018 | Bolea | G01J 1/42 |
| 2019/0104976 A1 | 4/2019 | Reynolds et al. | |
| 2020/0191727 A1* | 6/2020 | Brace | C12Q 1/66 |

FOREIGN PATENT DOCUMENTS

| | | |
|---|---|---|
| GB | 2 281 966 | 3/1995 |
| JP | 2008-239247 A2 | 10/2008 |
| JP | 2009-264821 | 11/2009 |
| WO | WO 1996/14570 | 5/1996 |
| WO | WO 1997/03209 | 1/1997 |
| WO | WO 1998/49544 | 11/1998 |
| WO | WO 1998/54578 | 12/1998 |
| WO | WO 2014/001982 | 1/2014 |
| WO | WO 2014/007846 | 1/2014 |
| WO | WO 2016/148867 | 9/2016 |
| WO | WO 2016/149017 | 9/2016 |

* cited by examiner

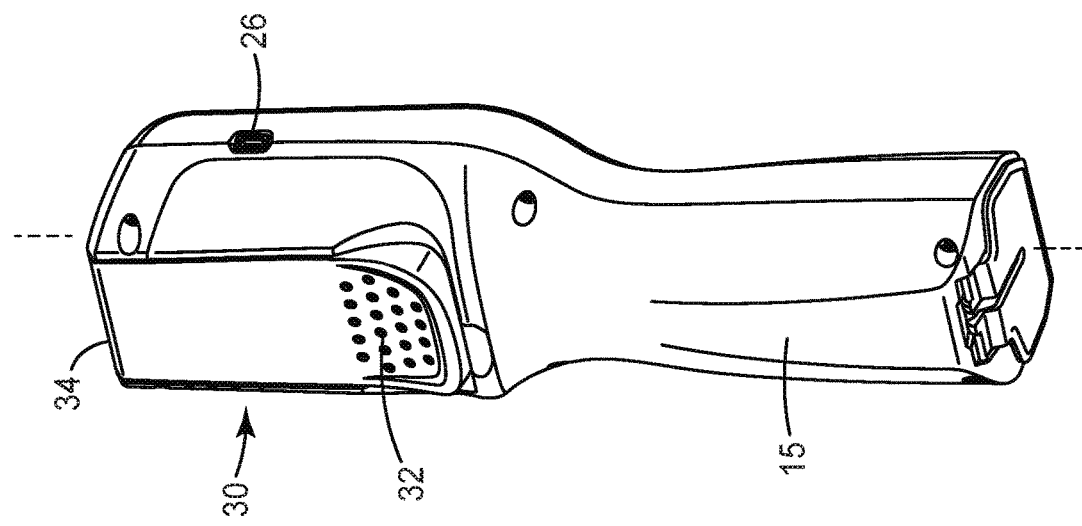
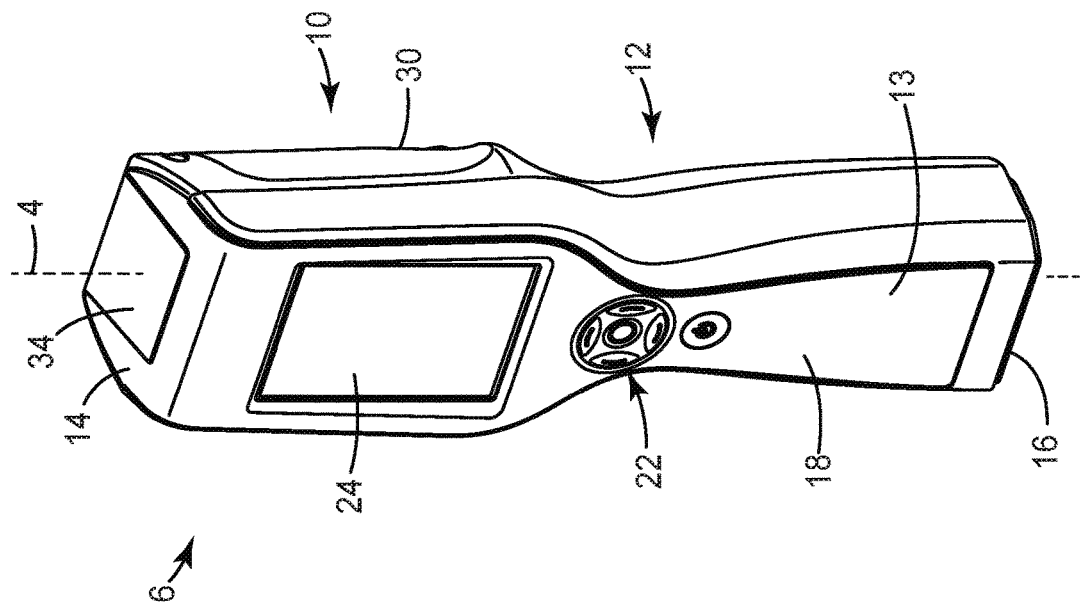

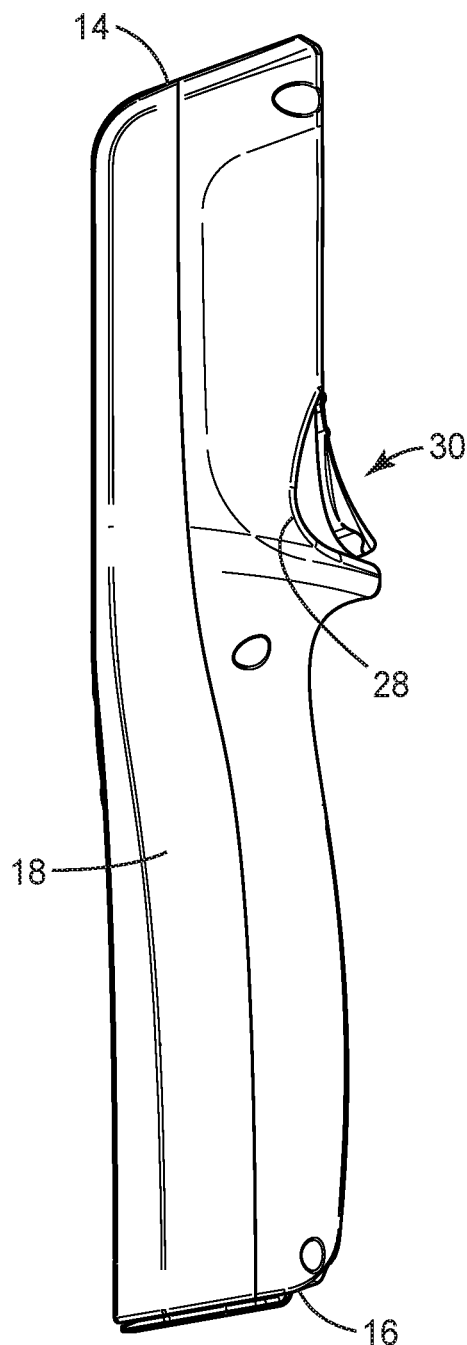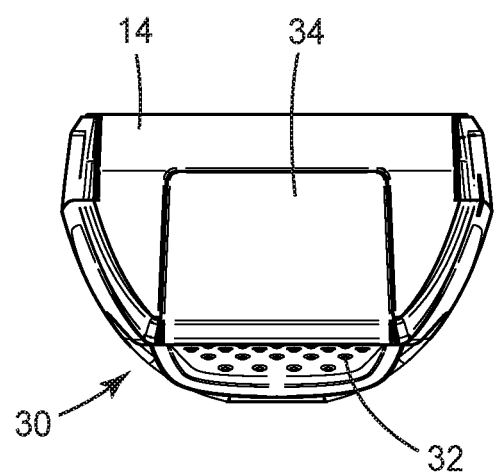
FIG. 3
FIG. 4

LIGHT DETECTION SYSTEM AND METHOD OF USING SAME

CROSS REFERENCE TO RELATED APPLICATIONS

This application is a continuation of U.S. application Ser. No. 15/557,904, filed Sep. 13, 2017, now pending, which is the § 371 U.S. National Stage of International Application No. of PCT/US2016/020548, filed Mar. 3, 2016, which claims the benefit of U.S. Provisional Application No. 62/132,790, filed Mar. 13, 2015, the disclosures of which are incorporated by reference in their entirety herein.

BACKGROUND

Sampling programs are used to monitor critical raw materials, in-process materials, finished goods, and processing environments in the food and beverage industry. Similar sampling programs are also used in healthcare settings to monitor the effectiveness of decontaminating environmental surfaces in a patient environment as well as instruments and devices used in screening and therapeutic procedures. Routine sampling and testing can allow quality assurance personnel to detect undesirable materials, such as microorganisms, at a very early stage and take steps to prevent subsequent contamination of equipment and/or products. A variety of tests can be performed to detect these undesirable materials. Examples of such tests include chemical residue tests (e.g., Adenosine triphosphate (ATP) bioluminescence tests and protein colorimetric tests), culture methods, genetic tests (e.g., PCR), immunodiagnostic tests, and bioluminescent tests.

Sample-collection devices or apparatuses are typically used to collect surface samples for environmental tests. Commercially-available sample-collection devices include absorbent devices such as sponges, swabs, and the like. In addition, certain sample-collection devices are capable of collecting a predetermined volume of a liquid sample.

Because of its use as energy "currency" in all metabolizing systems, ATP can indicate the presence of organic or bioorganic residues in a sample. The presence of ATP can be measured using a bioluminescent enzymatic assay. For example, a luciferin/luciferase enzyme assay system uses ATP to generate light. This light output can be detected and quantified in a light detection device, e.g., a luminometer. The presence of ATP in a sample may be a direct indicator of the presence of a microorganism (i.e., the ATP is derived from microorganisms in a sample containing no other sources of ATP), or the ATP may be an indirect indicator of the presence of a microorganism (i.e., the ATP is derived from vegetative or animal matter and indicates that nutrients that support the growth of microorganisms may be present in the sample). In addition, the presence or absence of ATP in a sample is used routinely to assess the efficacy of cleaning processes, e.g., in food, beverage, healthcare (e.g., environmental surfaces, surgical instruments, endoscopes, and other medical devices), water, and sanitation industries.

For example, ATP measurement systems have been utilized as monitoring tools in the food industry for over 15 years to audit the efficacy of sanitation processes. Such systems can detect very small amounts of ATP (e.g., 1 femtomole) on a variety of surfaces commonly found in food processing operations that need to be cleaned and disinfected. Detecting the presence of ATP on surfaces that are supposed to be sanitized can indicate a failure of the cleaning and disinfection process.

More recently, ATP monitoring tools have been adopted for a similar purpose in clinical applications to monitor the cleanliness of a patient's environment. There is now compelling clinical evidence that contaminated surfaces in a hospital make an important contribution to the epidemic and endemic transmission, e.g., of *C. difficile*, VRE, MRSA, *A. baumannii*, and *P. aeruginosa*, and to the endemic transmission of norovirus. Effective infection prevention programs include systematic monitoring of the environment's cleanliness. ATP monitoring, for example, can provide a quantitative measurement system that can be used to support such a program.

SUMMARY

In general, the present disclosure provides various embodiments of a light detection device and a method of using such device. In one or more embodiments, the light detection device can include a housing and a port formed in a top surface of the housing. The detection device can also include a door connected to the housing. In one or more embodiments, the door can include an actuator portion and a cover portion connected to the actuator portion. The actuator portion can be adapted to selectively move the door between a closed position and an open position. When in the closed position, the cover portion can be adapted to close the port. Further, when in the open position, the cover portion can be adapted to open the port to allow external access to the port. In one or more embodiments, the light detection device is adapted to allow a user to grasp a handle portion of the housing and, with the same hand, engage the actuator portion to selectively move the door between the closed position and the open position.

In one aspect, the present disclosure provides a light detection device that includes a housing including a top surface and a bottom surface, where the housing extends along a housing axis between the top surface and the bottom surface. The housing further includes a handle portion disposed between the top surface and the bottom surface. The device also includes a port formed in the top surface of the housing, where the port is adapted to receive a sample; and a door connected to the housing. The door includes an actuator portion adapted to selectively move the door between a closed position and an open position, and a cover portion connected to the actuator portion and adapted to close the port when the door is in the closed position and open the port when the door is in the open position to allow external access to the port. The light detection device is adapted to allow a user to grasp the handle portion with a hand and, with the same hand, engage the actuator portion to selectively move the door between the closed position and the open position.

In another aspect, the present disclosure provides a method that includes grasping a handle portion of a housing of a light detection device, where the light detection device further includes a top surface, a bottom surface, and a port formed in the top surface, where the handle portion is disposed between the top surface and the bottom surface. The method further includes engaging an actuator portion of a door connected to the housing to move the door from a closed position to an open position, where the door further includes a cover portion connected to the actuator portion that is adapted to close the port when the door is in the closed position and to open the port when the door is in the open position to allow external access to the port. The method further includes disposing a sample within the housing through the port, and engaging the actuator portion of the door to move the door from the open position to the closed position.

In another aspect, the present disclosure provides a light detection device that includes a housing including a top surface and a bottom surface, where the housing extends along a housing axis between the top surface and the bottom surface; a port formed in the top surface of the housing, wherein the port is adapted to receive a sample; and a door connected to the housing. The door includes a first end and a second end; an actuator portion adjacent the first end adapted to selectively move the door between a closed position and an open position; and a cover portion adjacent the second end connected to the actuator portion and adapted to close the port when the door is in the closed position and open the port when the door is in the open position to allow external access to the port. The actuator is adapted to rotate the door about a rotation axis that is substantially orthogonal to the housing axis. And the rotation axis is disposed between the first end and the second end of the door.

All headings provided herein are for the convenience of the reader and should not be used to limit the meaning of any text that follows the heading, unless so specified.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity but include the general class of which a specific example may be used for illustration. The terms "a," "an," and "the" are used interchangeably with the term "at least one."

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The use of the term "and/or" in certain portions of this disclosure is not intended to mean that the use of "or" in other portions cannot mean "and/or."

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIG. 1 is a schematic front perspective view of one embodiment of a light detection device including a door that is disposed in a closed position.

FIG. 2 is a schematic rear perspective view of the light detection device of FIG. 1 with the door of the device disposed in the closed position.

FIG. 3 is a schematic right-side view of the light detection device of FIG. 1 with the door of the device disposed in the closed position.

FIG. 4 is a top plan view of the light detection device of FIG. 1 with the door of the device disposed in the closed position.

DETAILED DESCRIPTION

Figure 6:
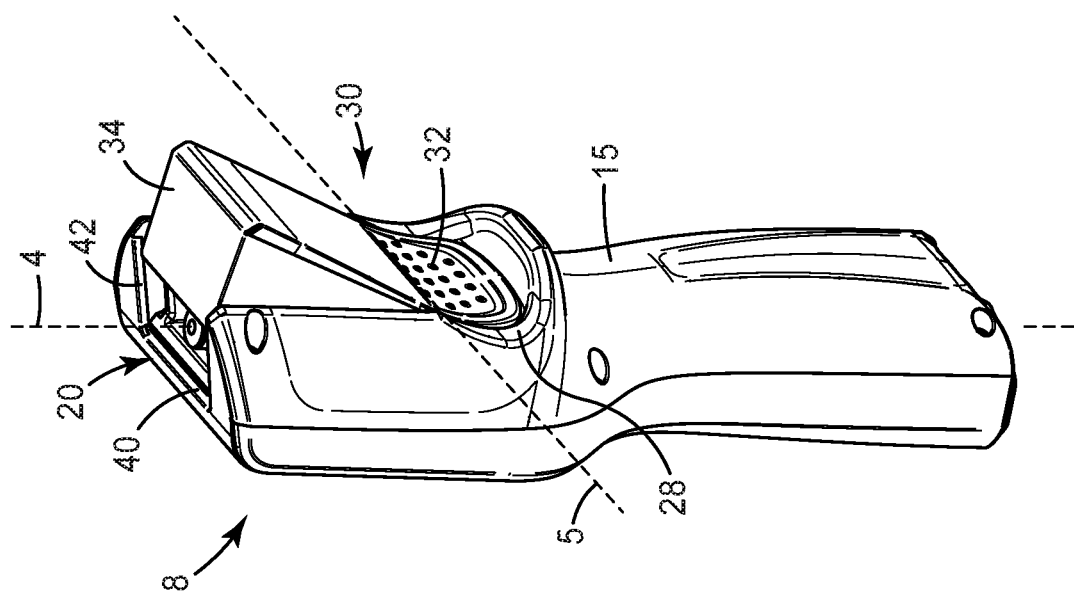
FIG. 6 is a schematic rear perspective view of the light detection device of FIG. 1 with the door of the device disposed in the open position.

In general, the present disclosure provides various embodiments of a light detection device and a method of using such device. In one or more embodiments, the light detection device can include a housing and a port formed in a top surface of the housing. The detection device can also include a door connected to the housing. In one or more embodiments, the door can include an actuator portion and a cover portion connected to the actuator portion. The actuator portion can be adapted to selectively move the door between a closed position and an open position. When in the closed position, the cover portion can be adapted to close the port. Further, when in the open position, the cover portion can be adapted to open the port to allow external access to the port. In one or more embodiments, the light detection device is adapted to allow a user to grasp a handle portion of the housing with a hand and, with the same hand, engage the actuator portion to selectively move the door between the closed position and the open position with the hand.

The light detection devices described herein can include any suitable device, e.g., luminometers, photometers (UV/visible), turbidimeters, colorimeters, fluorometers (e.g., portable devices that use light detection for environmental surface and water sampling, including both biological (microbial) testing and chemical content testing), etc. In one or more embodiments, a light detection device can include a light source (e.g., one or more light emitting diodes), a sample chamber, a light detector (e.g., a photomultiplier tube (PMT), a photodiode, etc.), and in some embodiments an optical system (including, e.g., one or more reflectors, filters, or lenses) to direct the light. In one or more embodiments, a test sample can emit light that is detected by a detector of the light detection device. Devices that detect light from a sample or detect the interaction of light with a sample can include one or more elements that block ambient light from interacting with the detector of the device, e.g., doors, gaskets, opaque housings, etc.

The light detection device can be utilized in any suitable application. For example, in one or more embodiments, the light detection device can be utilized to detect and measure light emitted by a sample disposed within the device. The sample can include any suitable sample, e.g., a bioluminescent sample. In one or more embodiments, the light detection device can detect the presence of ATP in a bioluminescent sample by analyzing light emitted by the sample that is produced by a luciferin-luciferase enzymatic reaction.

The accuracy and repeatability of currently available ATP detection systems can vary significantly. Such variability can be caused by difficulties in acquiring samples in a repeatable manner. Further, systems that employ a luciferin-luciferase detection chemistry can vary because of the lack of repeatability of how the reagent composition is formulated and the form factor employed to provide the reagents in an assay. In addition, the optical characteristics of the detection system can affect accuracy and repeatability. For example, some detection systems utilize a photomultiplier tube as the detector whereas other systems employ photodiodes. These detection systems can include a port that is connected to a detector disposed within a housing of the system. A sample can be disposed within the housing through the port. These ports, however, can allow ambient light to be transmitted into the detector, which can hinder accurate readings and potentially damage the detector. Some systems may include a door or cap that covers the port to prevent ambient light from being transmitted into the detector. These systems, however, may be awkward to operate as they may require one hand to grasp the system and the other to open and close the door that covers the port.

FIGS. 1-9 are various views of one embodiment of a light detection device 10. The light detection device 10 can include any suitable light detection device, e.g., a luminometer. In one or more embodiments, the device 10 can be part of a light detection system that can also include a sampling apparatus (not shown) that can be disposed within the device 10 and contain a sample. Any suitable sampling apparatus can be utilized, e.g., the sampling apparatuses described in PCT Patent Publication No. WO 2014/007846 and U.S. Patent Publication No. 2012/0329081.

The device 10 can include a housing 12 that can take any suitable shape or combination of shapes. In one or more embodiments, the housing 12 can take an ergonomic shape or combination of shapes that allows a user to grasp the housing and operate the device 10 with a single hand. Further, the housing 12 can be a single, unitary housing or can include two or more pieces, sections, or portions that are attached together using any suitable technique or combination of techniques. The housing 12 can extend along a housing axis 4 between a top surface 14 and a bottom surface 16. The housing 12 can also include an optional handle portion 18 disposed between the top surface 14 and the bottom surface 16. The handle portion 18 can include any suitable shape or combination of shapes. The housing 12 can also include a front surface 13 that extends between the top surface 14 and the bottom surface 16, and a back surface 15 that also extends between the top surface and the bottom surface.

The housing 12 can also include a port 20 disposed in the top surface 14 of the housing (FIGS. 5-7 and 9). Although illustrated as being disposed in the top surface 14, the port 20 can be disposed in any suitable surface of the housing 12, e.g., in the bottom surface 16, front surface 13, or back surface 15 of the housing. The port 20 can be adapted to allow a user to dispose a sample within the housing 12 such that light emitted by or interacting with the sample can be detected by a detector (not shown) disposed within the housing. The detector can be any suitable detector, e.g., the detectors described in cofiled U.S. Provisional Patent Application No. 62/132,774, filed Mar. 13, 2015. In one or more embodiments, the port 20 can be connected to the detector such that a sample can be disposed within the housing through the port and positioned within the housing such that the detector can measure one or more characteristics of the sample. For example, if the sample includes a photoluminescent sample, then the detector can be utilized to measure, e.g., an intensity of light emitted by the photoluminescent sample.

The port 20 can be adapted to receive a sample. The sample can be disposed within the housing 20 in any suitable manner. For example, in one or more embodiments, the sample can be directly disposed within the housing through the port 20. In one or more embodiments, the sample can be contained within a sampling apparatus that is adapted to be disposed within the housing by being inserted into the port 20. The port 20 can take any suitable shape or combination of shapes. In one or more embodiments, the port 20 can be adapted to receive a sampling apparatus.

In one or more embodiments, the port 20 can be connected to a receptacle (not shown) that is disposed within the housing 12. The receptacle can be adapted to receive a sampling apparatus and position the apparatus within the housing such that the detector can measure one or more characteristics of a sample disposed within the sampling apparatus. Any suitable receptacle can be utilized, e.g., one or more of the receptacles described in cofiled U.S. Provisional Patent Application No. 62/132,774, filed Mar. 13, 2015.

The light detection device 10 can also include one or more controls 22 that are adapted to provide an interface for the user to perform various functions with the device 12. Any suitable control or controls 22 can be provided with the device 10. Further, in one or more embodiments, the controls 22 can be disposed in any suitable location on or in the housing 12. For example, in the embodiment illustrated in FIG. 1, the controls 22 are disposed on or in a front surface 13 of the housing 12 such that a user can grasp the handle portion 18 of the housing 12 and operate the controls with a thumb or finger of the grasping hand. Such positioning of the controls 22 can allow operation of the device 10 with a single hand. The controls 22 can provide an interface for a user and can be electrically coupled to any suitable circuitry disposed within the housing 12 of the device 10. Such circuitry can include any suitable electronic device or devices, e.g., one or more controllers, processors, storage devices, power converters, analog/digital converters, GPS components, wireless antennas and receivers, etc. The circuitry can be electrically coupled to any suitable power source or sources, e.g., batteries, external power sources, etc. The circuitry can be connected to any suitable external device or power source through, e.g., one or more additional ports 26 disposed on or in the housing in any suitable location.

The device 10 can also include a display 24 that is adapted to provide a user with an interface with the circuitry disposed within the housing 12 of the device. The display 24 can be in any suitable location on or in the housing 12. In the embodiment illustrated in FIG. 1, the display 24 is disposed in the front surface 13 of the housing. The display 24 can include any suitable display. In one or more embodiments, the display 24 can be a touch-sensitive display that can provide the user with control of the device and can also display information to the user. Any suitable touch sensitive display 24 can be utilized with device 10.

The light detection device 10 can also include a door 30. The door 30 can be connected to the housing 12 of the device 10 using any suitable technique or combination of techniques. The door 30 can include any suitable material or combination of materials. In one or more embodiments, the door 30 includes the same material or combination of materials as the housing 12 of the device 10. Further, the door 30 can take any suitable shape or combination of shapes and have any suitable dimensions.

In one or more embodiments, the door 30 can include an actuator portion 32 and a cover portion 34 connected to the actuator portion. In one or more embodiments, the actuator portion 32 can be integral with the cover portion 34, or the actuator portion and the cover portion can be separate elements that are connected using any suitable technique or combination of techniques. For example, in one or more embodiments, the actuator portion 32 and the cover portion 34 can be connected by a hinge (e.g., hinge 36 of FIG. 7).

Figure 5:
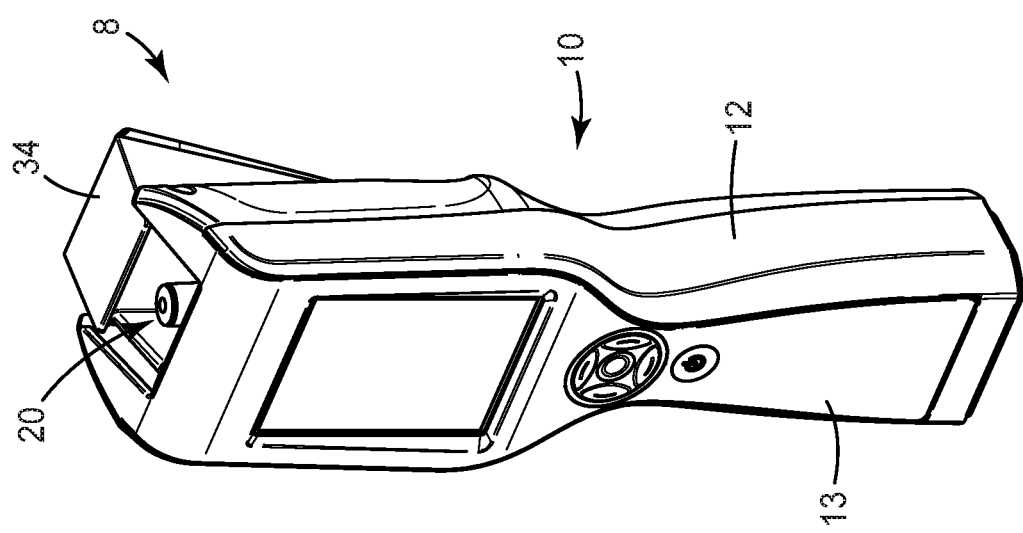
FIG. 5 is a schematic front perspective view of the light detection device of FIG. 1 when the door of the device is disposed in an open position.
Figure 9:
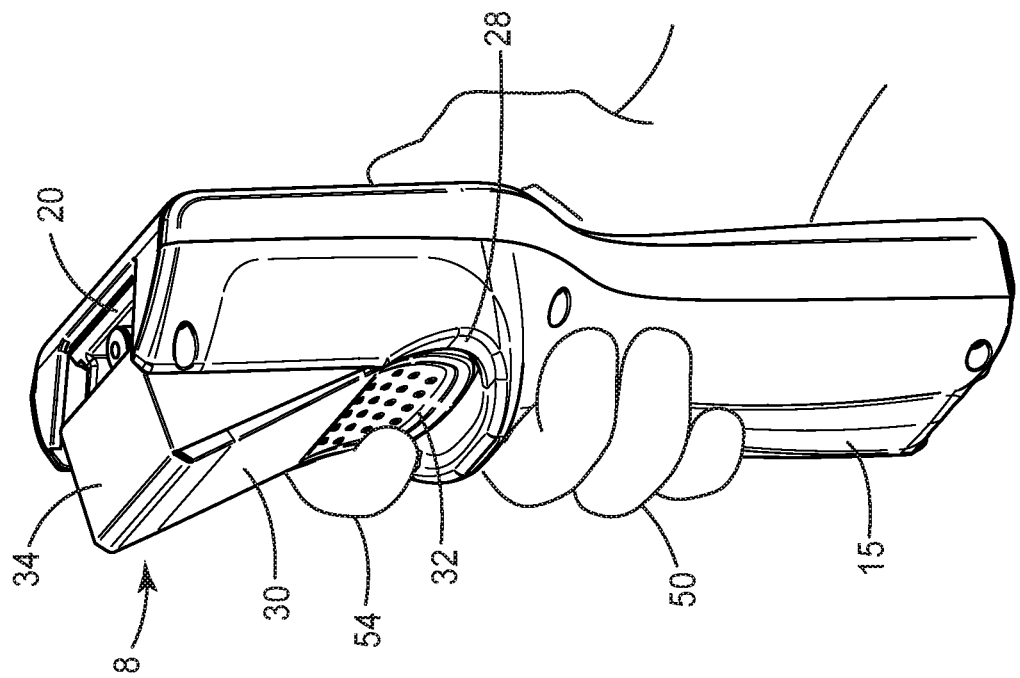
FIG. 9 is a schematic left-side view of the light detection device of FIG. 1 grasped by the hand of the user and the door of the device disposed in the open position.

The door 30 can be adapted such that it can be disposed in a closed position or an open position. For example, FIGS. 1-4 and 8 are various views of the device 10 when the door 30 is disposed in a closed position 6. Further, for example, FIGS. 5-6 and 9 are various views of the device 10 when the door is disposed in an open position 8. The door 30 can be disposed in the closed position 6 or the open position 8 using any suitable technique or combination of techniques. For example, in one or more embodiments, the actuator portion 32 is adapted to selectively move the door 30 between the closed position 6 and the open position 8. Further, in one or more embodiments, the cover portion 34 of door 30 is adapted to close the port 20 when the door is in the closed position 6 and open the port when the door is in the open position 8. When in the open position 8, the cover portion 34 can allow external access to the port 20.

Figure 7:
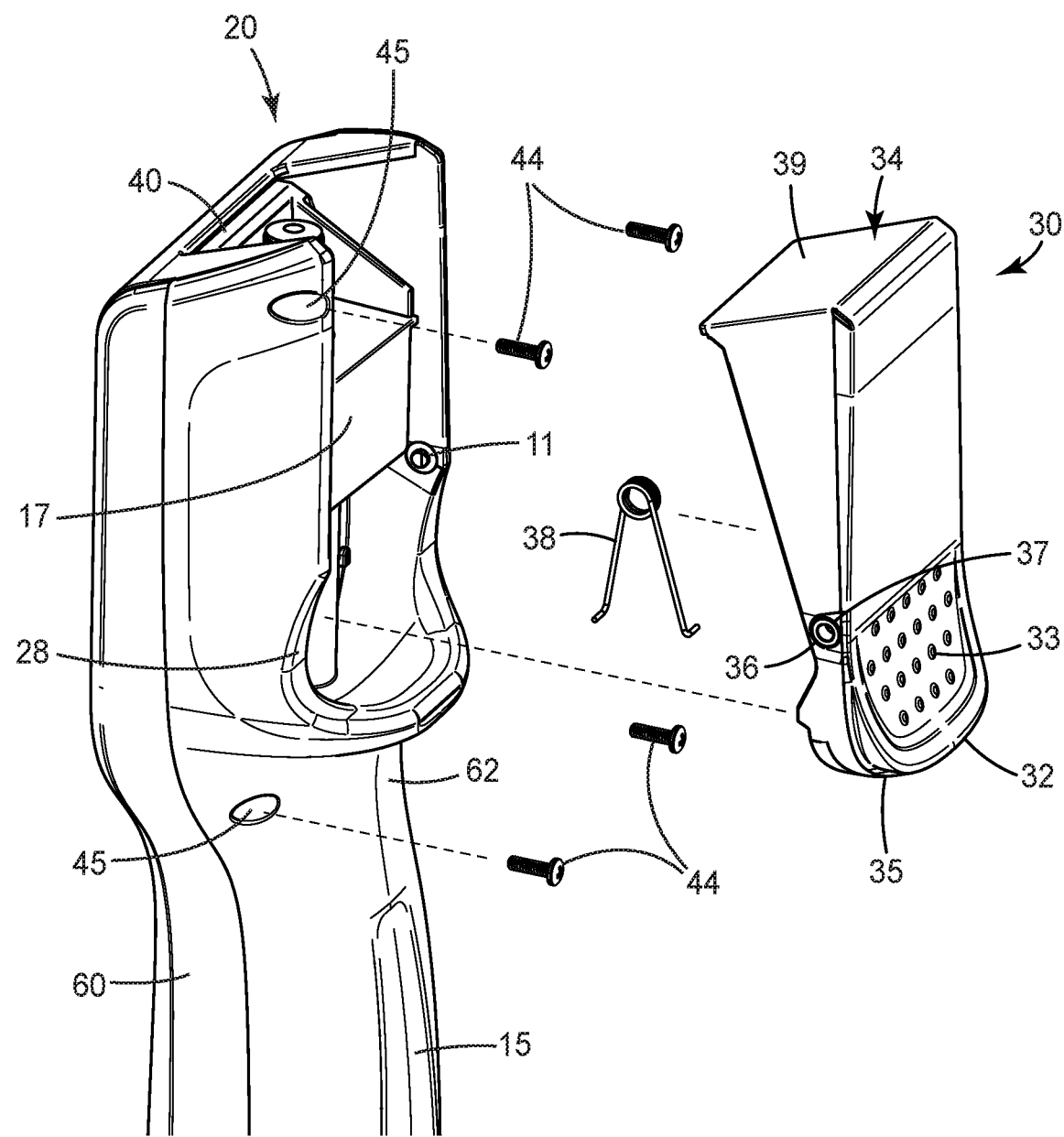
FIG. 7 is a schematic exploded view of a portion of the light detection device of FIG. 1.

The door 30 can be connected to the housing 12 of device 10 using any suitable technique or combination of techniques. For example, in one or more embodiments, the door 30 can be attached to the housing 12 by a hinge 36 as shown in FIG. 7. The hinge 36 can be any suitable hinge. In the embodiment illustrated in FIG. 7, the hinge 36 includes a protuberance 37 that is adapted to be disposed within an opening 11 formed in the housing 12. The door 30 can include any suitable number of protuberances 37 such that the hinge 36 attaches the door to the housing 12. In one or more embodiments, the hinge 36 can be attached to the housing 12 by inserting the protuberance 37 into the opening 11 disposed in one or both of two sections 60, 62 of the housing 12. The sections 60, 62 of the housing 12 can be secured together by screws 44 that are inserted through openings 45. The hinge 36 can be disposed in any suitable location on or in the housing 12 and in any suitable orientation relative to the housing axis 4.

Further, in one or more embodiments, a spring 38 can be disposed between the door 30 and the housing 12. Any suitable spring can be utilized. The spring 38 is adapted to allow the door 30 to pivot between the closed position 6 and the open position 8. In one or more embodiments, the door 30 can be biased in either the closed position 6 or the open position 8. In the embodiment illustrated in FIG. 7, the spring 38 biases the door 30 in the closed position 6 such that the port 20 is closed to the external environment. By biasing the door 30 in the closed position 6, the cover portion 34 can protect the port 20 and prevent ambient light or other environmental elements (e.g., moisture) from entering the interior of the housing 12 through the port. When in the closed position 6, the cover portion 34 can also prevent ambient light from entering a detector disposed within the housing.

In one or more embodiments, the actuator portion 32 of the door 30 is adapted to rotate the door about a rotation axis 5 as shown in FIG. 6. The rotation axis 5 can be oriented in any suitable relationship to the housing axis 4. For example, in one or more embodiments, the rotation axis 5 can be substantially orthogonal to the housing axis 4 as shown in FIG. 6. As used herein, the phrase "substantially orthogonal" means that the rotation axis 5 is disposed such that an angle of between 85° to 95° is formed with the housing axis 4. In one or more embodiments, the rotation axis 5 can be aligned with the hinge 36 (FIG. 7).

The actuator portion 32 of door 30 is adapted to selectively move the door from the closed position 6 to the open position 8. Further, the actuator portion 32 can take any suitable shape or combination of shapes. In one or more embodiments, the actuator portion 32 can take a curved shape such that it is adapted to receive a finger of a hand of a user. Further, in one or more embodiments, the actuator portion 32 can include a textured surface 33 such that the user can more easily engage the actuator portion to place the door either in the closed position 6 or the open position 8.

The actuator portion 32 can be disposed in any suitable relationship relative to the housing 12. In one or more embodiments, the actuator portion 32 can be disposed adjacent the handle portion 18 of the housing 12. As used herein, the phrase "adjacent the handle portion" means that the actuator portion 32 is disposed closer to the handle portion 18 than to either the top surface 14 or the bottom surface 16 of the housing 12. The actuator portion 32 can be disposed adjacent the handle portion 18 such that the user can grasp the handle portion and engage the actuator portion with a single hand. In other words, the light detection device 10 can be adapted to allow a user to grasp the handle portion 18 with a hand and, with the same hand, engage the actuator portion 32 to selectively move the door 30 between the closed position 6 and the open position 8.

Connected to the actuator portion 32 is the cover portion 34. In one or more embodiments, the cover portion 34 is adapted to close the port 20 when the door 30 is in the closed position 6 and open the port when the door is in the open position 8 to allow external access to the port. In one or more embodiments, the cover portion 34 of the door 30 is adapted to minimize the amount of ambient light entering the port 20 when the door is in the closed position 6. In one or more embodiments, the door 30 is adapted to prevent substantially all ambient light from entering the port 20 when the door is in the closed position 6. In one or more embodiments, the door 30 is adapted to block a sufficient amount of ambient light from entering the housing 12 such that the ability to detect and measure a light signal associated with the sample is not compromised.

The cover portion 34 can be disposed in any suitable relationship relative to the housing 12. In one or more embodiments, the cover portion 34 is disposed such that it forms a portion of the top surface 14 of the housing 12. In one or more embodiments, the cover portion 34 can be level or flush with the top surface 14 of the housing 12 when the door 30 is in the closed position 6.

In one or more embodiments, the port 20 can include a ledge 40 that is adapted to engage the cover portion 34 when the door 30 is in the closed position 6. The ledge 40 can take any suitable shape or combination of shapes. Further, the ledge 40 can be disposed along an entire perimeter of the port 20 or along any suitable portion of the perimeter of the port. The combination of the cover portion 34 and ledge 40 can prevent ambient light from entering the port 20 when the door 30 is in the closed position 6.

In one or more embodiments, the port 20 can also include a gasket (not shown) that is disposed between the cover portion 34 and the ledge 40. The gasket can extend along any suitable portion of the ledge 40 of the port 20. In one or more embodiments, the gasket extends the entire ledge 40. The gasket, ledge 40, and the cover portion 34 can combine to prevent ambient light from entering the port 20. Further, in one or more embodiments, the gasket can also provide a seal between the cover portion 34 and the ledge 40 to prevent external environmental elements from entering the port 20, e.g., moisture. Further, one or more of the gasket, ledge 40, and cover portion 34 can prevent a sample disposed within the housing 12 from undesirably leaking out of the housing.

In one or more embodiments, the port 20 can also include an overhang (not shown) that covers any space between the top surface 14 and the cover portion 32 when the door 30 is in the closed position 6. The overhang can take any suitable shape and be located in any suitable location. In one or more embodiments, the overhang can be connected to the top surface 14 and/or the cover portion 34.

The door 30 can also include a first end 35 and a second end 39 (FIG. 7). In one or more embodiments, the actuator portion 32 is adjacent the first end 35 and the cover portion 34 is adjacent the second end 39. As used herein, the phrase "adjacent the first end" means that the actuator portion 32 is disposed closer to the first end 35 of the door 30 than to the second end 39 of the door. Similarly, the phrase "adjacent the second end" means that the cover portion 34 is disposed closer to the second end 39 of the door than to the first end 35.

As mentioned herein, the rotation axis 5 can be disposed at any suitable location relative to the door 30. In one or more embodiments, the rotation axis 5 can be disposed between the first end 35 and the second end 39 of the door 30. In one or more embodiments, the rotation axis 5 is disposed at approximately a midpoint between the first end 35 and the second end 39 of the door 30. As used herein, the term "approximately" means that the rotation axis 5 is disposed within 1 cm of the midpoint between the first end 35 and the second end 39 of the door 30. In one or more embodiments, the rotation axis 5 is disposed closer to the first end 35 of the door 30 than to the second end 39. Further, in one or more embodiments, the rotation axis 5 is disposed closer to the second end 39 of the door 30 than to the first end 35.

In one or more embodiments, the rotation axis 5 is disposed closer to the midpoint between the first and second ends 35, 39 of the door 30 than to either the first end or the second end of the door. In one or more embodiments, the rotation axis 5 is disposed about halfway between the midpoint located between the first and second ends 35, 39 of the door 30 and the first end. In one or more embodiments, the rotation axis 5 is disposed about halfway between the midpoint located between the first and second ends 35, 39 of the door 30 and the second end.

In one or more embodiments, the actuator portion 32 can be defined as a portion of the door 30 disposed between the rotation axis 5 and the first end 35. Further, in one or more embodiments, the cover portion 34 of the door 30 can be defined as a portion of the door disposed between the rotation axis 5 and the second end 39 of the door. The actuator portion 32 can include any suitable portion of door 30, e.g., no greater than about 90%, no greater than about 80%, no greater than about 70%, no greater than about 60%, no greater than about 50%, etc. In one or more embodiments, the actuator portion 32 can be at least about 5%, at least about 10%, at least about 20%, at least about 30%, at least about 40%, at least about 50% of the door 30. Further, the cover portion 34 of door 30 can include any suitable portion of the door, e.g., no greater than about 90%, no greater than about 80%, no greater than about 70%, no greater than about 60%, no greater than about 50%, etc. In one or more embodiments, the door portion 34 can be at least about 5%, at least about 10%, at least about 20%, at least about 30%, at least about 40%, at least about 50% of the door 30.

The light detection device 10 can also include a switch (not shown) that is coupled to the door 30 and adapted to activate circuitry and/or a detector disposed within the housing (not shown) when the door is disposed in the closed position 6. Any suitable switch or combination of switches can be utilized. Further, in one or more embodiments, the switch can deactivate circuitry and/or a detector disposed within the housing 12 when the door 30 is disposed in the open position 8 to prevent ambient light from damaging the detector. The switch can be disposed in any suitable position relative to the door 30. In one or more embodiments, the switch can be positioned between the actuator portion 32 and the housing 12.

As mentioned herein, the door 30 can be disposed in any suitable location relative to the housing 12. In one or more embodiments, the door 30 is disposed such that the actuator portion 32 is adjacent the back surface 15 of the housing. As used herein, the phrase "adjacent the back surface" means that the actuator portion 32 is disposed closer to the back surface 15 of housing 12 than to the front surface 13. In one or more embodiments, the back surface 15 of the housing 12 can include a recessed portion 17 that is adapted to receive the door 30 as illustrated in FIG. 7. In one or more embodiments, the door 30 can sit within the recessed portion 17 of the back surface 15 such that an outer surface of the door is level or flush with the adjacent back surface.

In one or more embodiments, the door can be disposed on a side surface of the housing 12 between the front surface 13 and the back surface 15. Further, in one or more embodiments, the door 30 can be disposed on the front surface 13 of the housing 12 adjacent the display 24 such that a user can engage the actuator portion 32 of the door with the thumb of the grasping hand. In such embodiments, the door 30 can include an opening or openings such that the user can access the controls 22 and view the display 24 through the door. In one or more embodiments, the door 30 can be disposed on the front surface 13 of the housing 12 on either side of the display 24 such that the user can access the controls 22 and view the display 24.

The back surface 15 can also include a finger receiving region 28 adjacent the actuator portion 32 of the door 30 (FIG. 6). As used herein, the phrase "adjacent the actuator portion" means that the finger receiving region 28 of the housing 12 is disposed closer to the actuator portion 32 than to the cover portion 34 of door 30. The finger receiving region 28 is adapted to receive one or more fingers of a user's hand when the user grips the handle portion 18 of the light detection device 10. The finger receiving region 28 is shaped such that a finger of a user can engage the actuator portion 32 of the door 30 and engage the actuator portion to move the cover portion 34 between the closed position 6 and the open position 8. In one or more embodiments, when the actuator portion 32 is engaged such that the door 30 is moved to the open position 8, the finger receiving region 28 accommodates a finger of a user to allow the finger to hold the actuator portion against the recessed portion 17 of the back surface 15 of the housing 12. In one or more embodiments, the finger receiving region 28 takes a shape that is complementary with the shape of the actuator portion 32 when the actuator portion is engaged and the door 30 is in the open position 8 as illustrated in FIG. 6.

Figure 8:
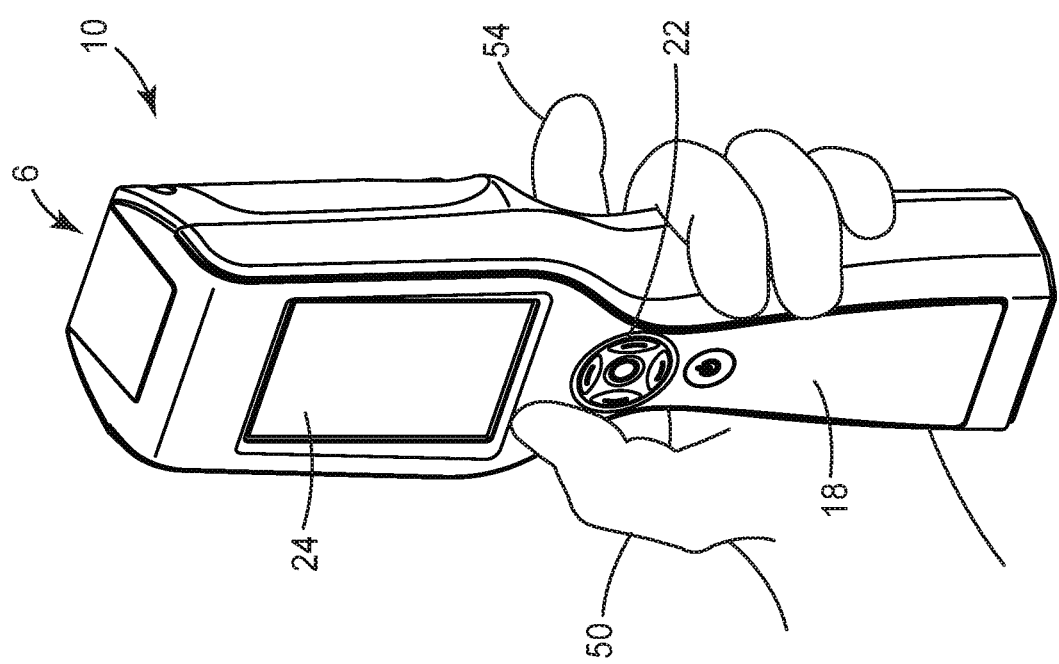
FIG. 8 is a schematic front view of the light detection device of FIG. 1 grasped by a hand of a user and the door of the device disposed in the closed position.
Figure 10:
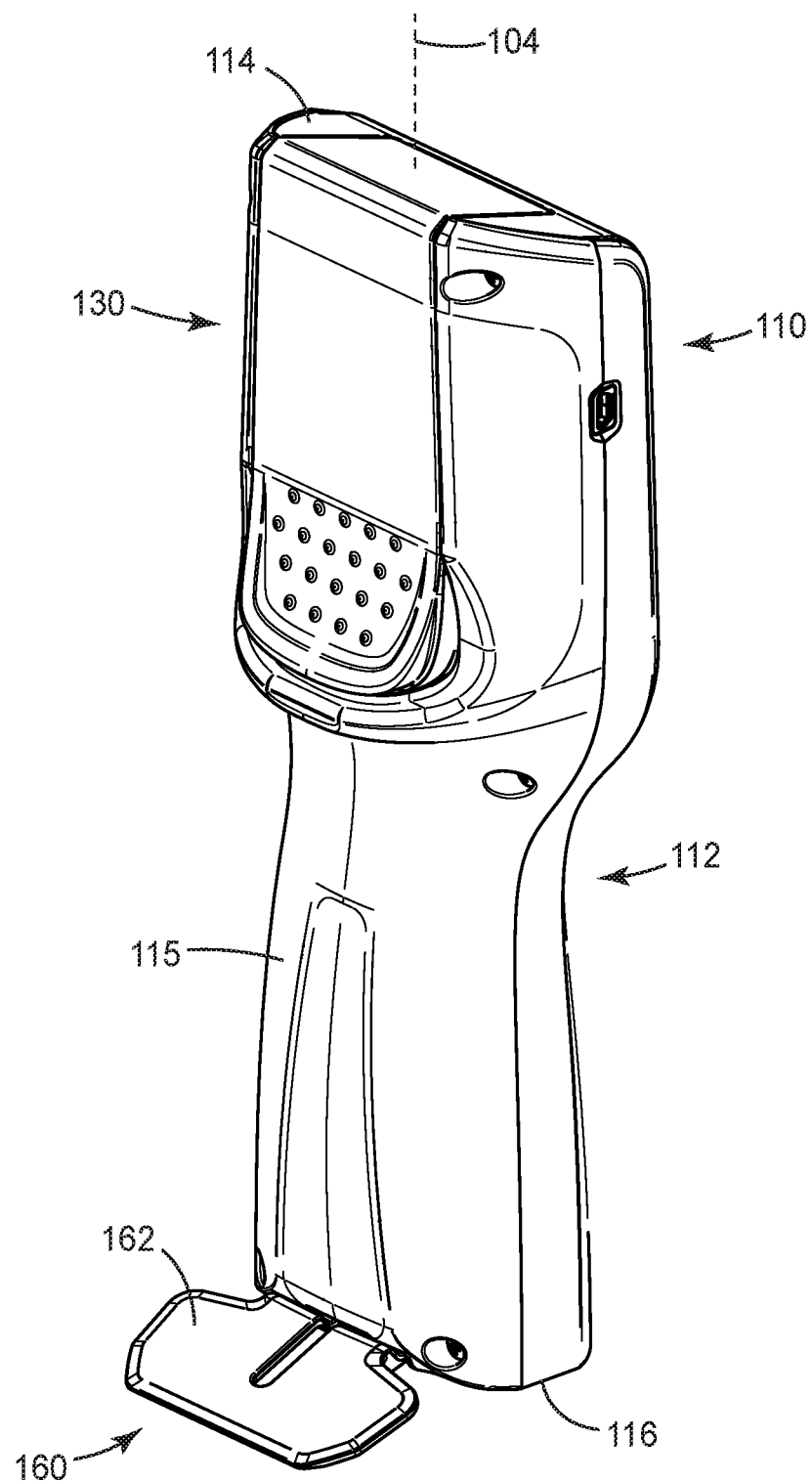
FIG. 10 is a schematic rear perspective view of another embodiment of a light detection device including a support member that is disposed in an open position.

The light detection device 10 can be utilized in any suitable manner to measure one or more characteristics of a sample disposed within the housing 12 of the device. For example, FIGS. 8-9 illustrate one technique for utilizing the device 10. As illustrated, a hand 50 of the user is shown in FIG. 8 grasping the handle portion 18 of the device 10. The hand 50 can engage the actuator portion 32 of the door 30 to move the door between the closed position 6 (FIG. 8) and the open position 8 (FIG. 9). When in the open position 8, the cover portion 34 opens the port 20 to allow external access to the port. In one or more embodiments, the user can engage the actuator portion 32 of the door 30 by pressing the actuator portion with a finger or thumb 54 of the hand 50 that is grasping the handle portion 18 of the housing 12. Engaging the actuator portion 32 can cause the door 30 to rotate about the rotation axis 5 to the open position 8. In one or more embodiments where the door 30 is biased in the closed position 6, pressing the actuator portion 32 of the door 30 opens the door, i.e., places the door in the open position 8.

When the door 30 is in the open position 8 as shown in FIG. 9, a sample or a sampling apparatus can be disposed within the housing 12 through the port 20, e.g., into a receptacle disposed within the housing. While the sample is being disposed within the housing 12, the finger or thumb 54 of the hand 50 of the user can maintain a force on the actuator portion 32 of the door 30 to keep the door in the open position 8.

In one or more embodiments, a latch (not shown) can be attached to the housing 12. The latch can be adapted to hold the door 30 in the open position 8 such that the user's finger can be disengaged from the actuator portion without the door returning to the closed position 6. Any suitable latch can be utilized. In embodiments where a latch is included, the door 30 can be moved from the open position 8 to the closed position 6 by engaging the actuator portion 32 of the door by applying a force to the actuator portion in a direction toward the interior of the housing 12, thereby releasing the door from the latch. Once the latch is released, the biasing of the door 30 will return the door to the closed position 6 when the user reduces the force applied to the actuator portion 32. In one or more embodiments, the user can move the door 30 from the open position 8 to the closed position 6 by releasing the actuator portion 32 such that the biasing of the door returns the door to the closed position 6 and the cover portion 34 of the door closes the port 20 of the housing 12.

In one or more embodiments, the device 10 can include a switch that activates circuitry disposed within the housing when the sample is disposed within the housing and the door is in the closed position 6. The circuitry can be activated by the switch using any suitable technique or combination of techniques. One or more characteristics of the sample can be measured after the door 30 has been moved from the open position 8 to the closed position 6. Any suitable characteristic or characteristics of the sample can be measured, e.g., intensity of light emitted by the sample.

In one or more embodiments, the detection device 10 can also include a tilt detection component (not shown) that can, in one or more embodiments, measure a tilt angle of the detection device 10. As used herein, the term "tilt angle" means an angle formed between the housing axis 4 and a vertical axis. As used herein, the term "vertical axis" refers to an axis that is aligned with the Earth's gravitational field. The tilt detection component can provide feedback to a user when the device 10 is positioned within a proper tilt angle and/or when the device is positioned at an improper tilt angle. Such feedback can be provided to the user using any suitable technique or combination of techniques, e.g., the feedback can be provided as a readout on the display 24, or the device 10 can be adapted to provide haptic feedback to the user. For example, during detection of light emitted by a sample, the user can be warned by an on-screen message on display 24, or the device 10 can provide haptic feedback, when the instrument is not being held at the correct tilt angle and/or when the instrument is being held at the correct tilt angle. On-screen instructions can be provided to the user to reorient the device 10 such that it is positioned within the correct tilt angle. The tilt detection component can be utilized to indicate to a user any suitable tilt angle or range of tilt angles. In one or more embodiments, a desirable tilt angle can be determined, e.g., by the quantity of a sample disposed within the housing, and by the optical properties and configurations of the detector within the housing. In general, the tilt angle can be selected to provide the most accurate detection of one or more characteristics of a sample disposed within the housing.

The tilt detection component can include any suitable circuitry or elements that can determine an orientation of the device 10 relative to the vertical axis. For example, in one or more embodiments, the tilt angle can be measured by a tilt sensor that is sampled by a microprocessor disposed either within the housing 12 of the device 10 or external to the housing 10 and coupled to the tilt sensor either wirelessly or through a wired coupling. Data provided by the tilt sensor can be averaged or normalized to yield a stable approximation of the tilt angle of the device 10 prior to or during analysis of the sample. The tilt detection component can be calibrated to have any suitable accuracy. For example, in one or more embodiments, the tilt detection component can be calibrated such that it provides, e.g., a 20% tilt angle measurement accuracy.

A calibrated 3M Clean-Trace™ NG Luminometer (commercially available from 3M Company, St. Paul, Minn.) was used to measure light in relative light units (RLUs) emitted by several bioluminescence samples disposed in several different sampling apparatuses. The Luminometer was fixtured in a holder for stability and repeatability of tilt angles during the test. The following tilt angles were measured: 0 degrees (vertical), 45 degrees (a commonly observed viewing angle used by users to maximize display contrast), and 90 degrees (simulates the Luminometer resting horizontally on a work surface). These three states were cycled through two times and return to vertical. A plurality of RLU readings was automatically acquired in each angle state to average out temporal variation and assay decay. The Luminometer was controlled by a computer running an RLU data logging program with a sample interval of 20 seconds.

Figure 18:
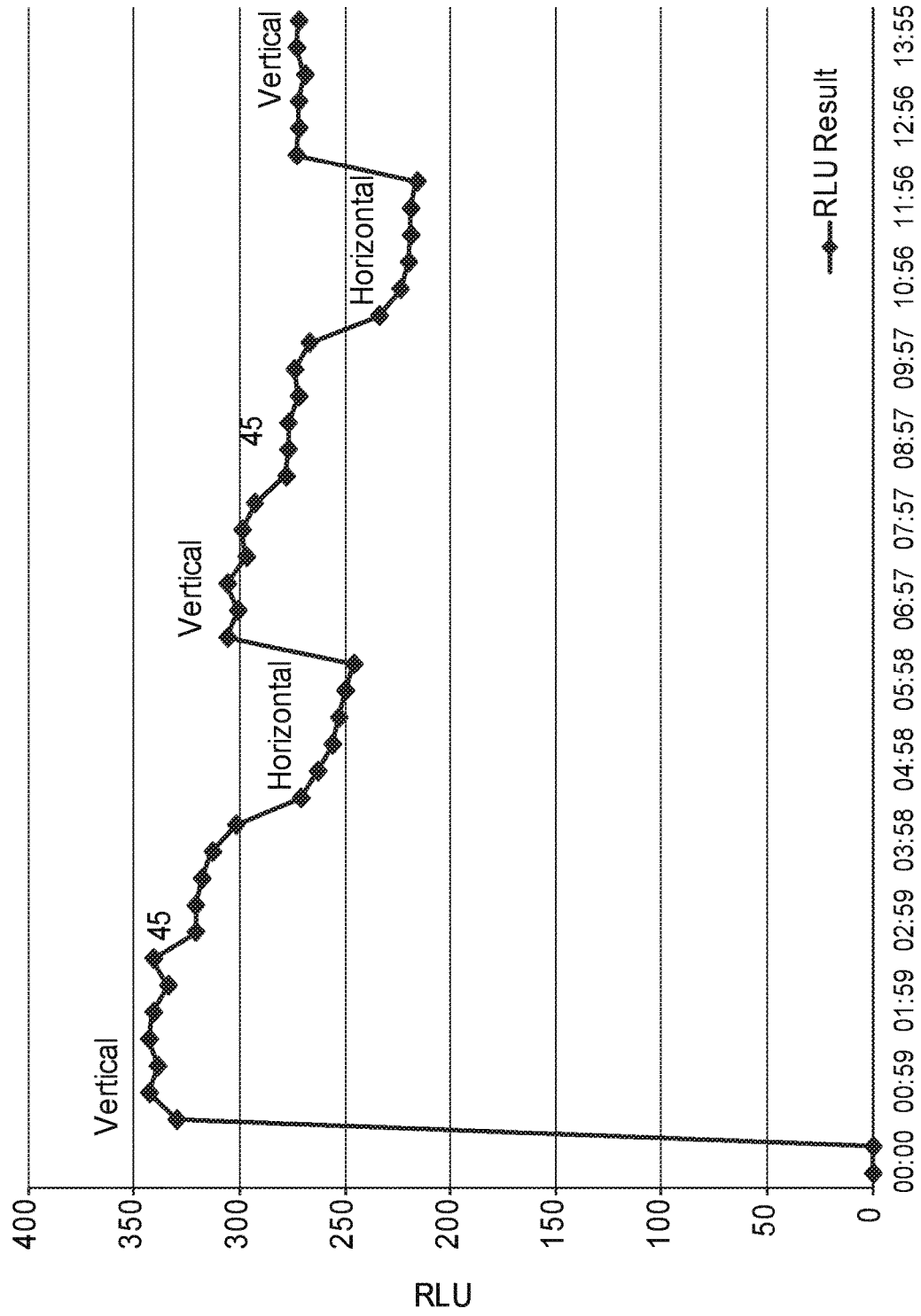
FIG. 18 is a graph of relative light units (RLUs) versus time as related to tilt angle for several supply apparatuses disposed at various tilt angles.

FIG. 18 is a graph of RLUs versus time that illustrates RLUs relative to various tilt angles that were measured. Tilt angles of 45 degrees typically reduced RLU readings by 10%. Tilt angles of 90 degrees typically reduced RLU readings by 25%.

While not wishing to be bound by any particular theory, measuring a sample with an instrument not held at the appropriate angle can yield a measured value difference greater than 20% relative to the real value because the sample being measured can typically be a small volume (less than 1 mL) liquid sample disposed in a cuvette portion of the sampling apparatus, where the sample can have an appreciable meniscus. When the device is held in an improper angle, at least a portion of the sample can be disposed outside of a light cavity of the detection device of the system that directs light to a detector, thereby reducing a volume of the sample that can emit light into the light cavity and, therefore, potentially yielding an erroneous signal. This tilt can, therefore, affect the radiance of the sample being analyzed.

In one or more embodiments, the tilt detection component can also be utilized to measure customer usage behaviors and abuse events that can be useful in predicting desired service intervals or provide training and guidance. Further, one or more embodiments of the tilt detection component can provide real-time mathematical normalization of RLU data based on measured tilt angle. This algorithm may be constrained to practical tilt angle limits. For example, measured angles greater than 90 degrees would prompt an immediate warning and suppress a normalization algorithm. In one or more embodiments, providing a user feedback on the tilt angle can allow the user to maintain the same tilt angle across multiple samples, thereby allowing for more consistent readings from sample to sample and from sampling period to sampling period.

Any suitable technique or combination of techniques can be utilized to maintain the light detection device 10 in a position having a desired tilt angle. For example, in one or more embodiments, a support member or members can be connected to the housing of the device such that the device can be placed on a working surface at the desired tilt angle.

For example, FIGS. 10-14 are various views of one embodiment of a light detection device 110. All of the design considerations and possibilities regarding the light detection device 10 of FIGS. 1-9 apply equally to the light detection device 110 of FIGS. 10-14. The light detection device 110 includes a housing 112 that extends along a housing axis 104 between a top surface 114 and a bottom surface 116. The housing 112 also includes a front surface 113 that extends between the top surface 114 and the bottom surface 116, and a back surface 115 that also extends between the top surface and the bottom surface.

One difference between light detection device 110 and device 10 of FIGS. 1-9 is that device 110 includes a support member 160. Support member 160 can be connected to the housing 112 in any suitable location and using any suitable technique or combination of techniques. In one or more embodiments, the support member 160 is integral with the housing 112. In one or more embodiments, the support member 160 is attached to the housing 112 and can be removed from the housing without damaging either the housing or the support member.

Figure 12:
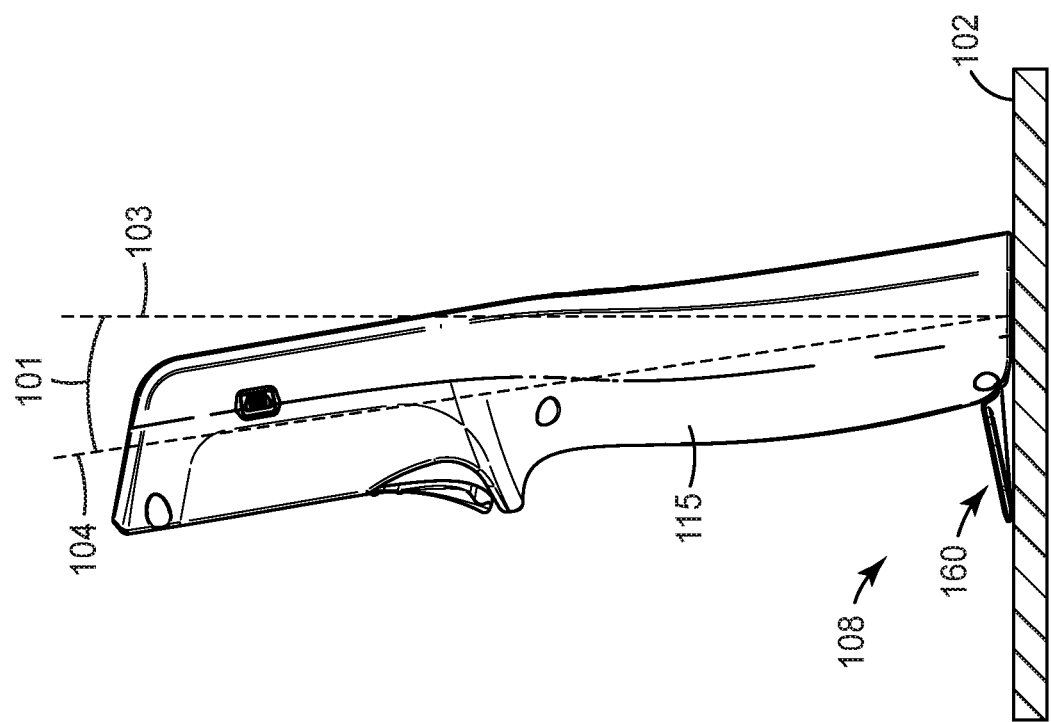
FIG. 12 is a schematic left-side view of the light detection device of FIG. 10 disposed on a working surface and the support member disposed in the open position.
Figure 11:
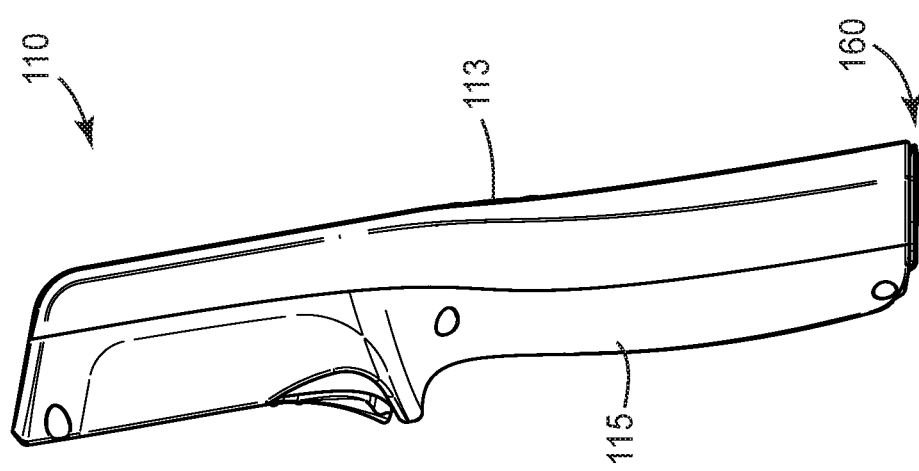
FIG. 11 is a schematic left-side view of the light detection device of FIG. 10 with the support member disposed in a closed position.
Figure 13:
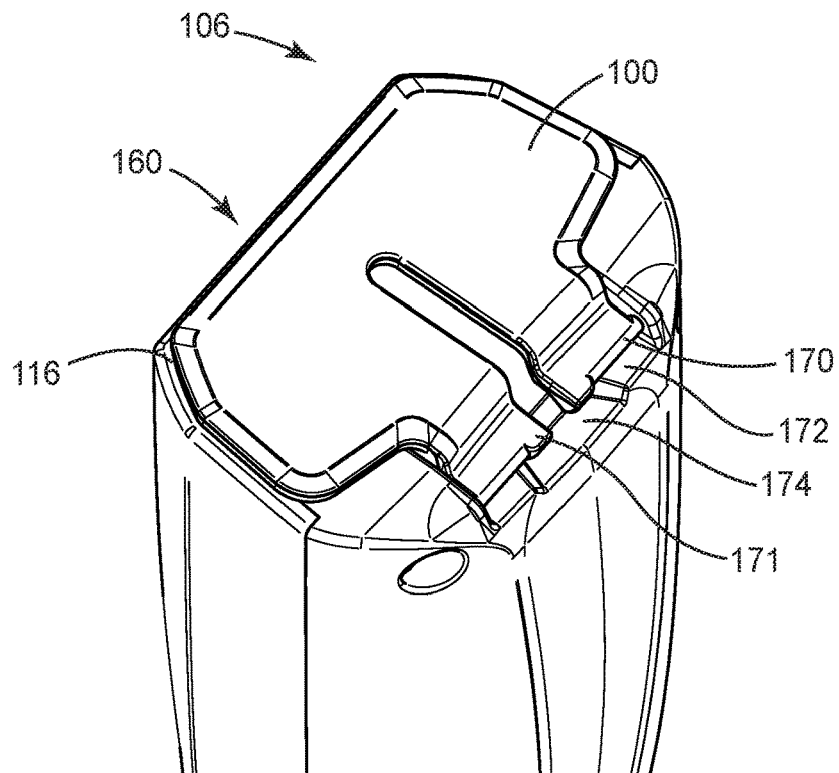
FIG. 13 is a schematic bottom perspective view of a portion of the light detection device of FIG. 10 with the support member disposed in the closed position.

In the embodiment illustrated in FIGS. 10-14, the support member 160 is connected to the housing 112 adjacent the bottom surface 116. As used herein, the phrase "adjacent the bottom surface" means that the support member 160 is connected to the housing 112 closer to the bottom surface 116 than to the top surface 114. The support member 160 can be connected to the housing 112 using any suitable technique or combination of techniques. For example, FIG. 13 is a schematic perspective view of the bottom surface 116 of the housing 112. The support member 160 in the illustrated embodiment is attached to the bottom surface 116 via a hinge 170. The hinge 170 can include any suitable hinge. In one or more embodiments, the hinge 170 can be a living hinge. Further, in one or more embodiments, the hinge 170 can be a ratcheted hinge that includes teeth 171 formed in the bottom surface 116 of the housing 112 that engage one or more notches 173 formed in the hinge. The ratcheted hinge 170 can be adapted to allow adjustment of the positioning of the support member 160.

Figure 14:
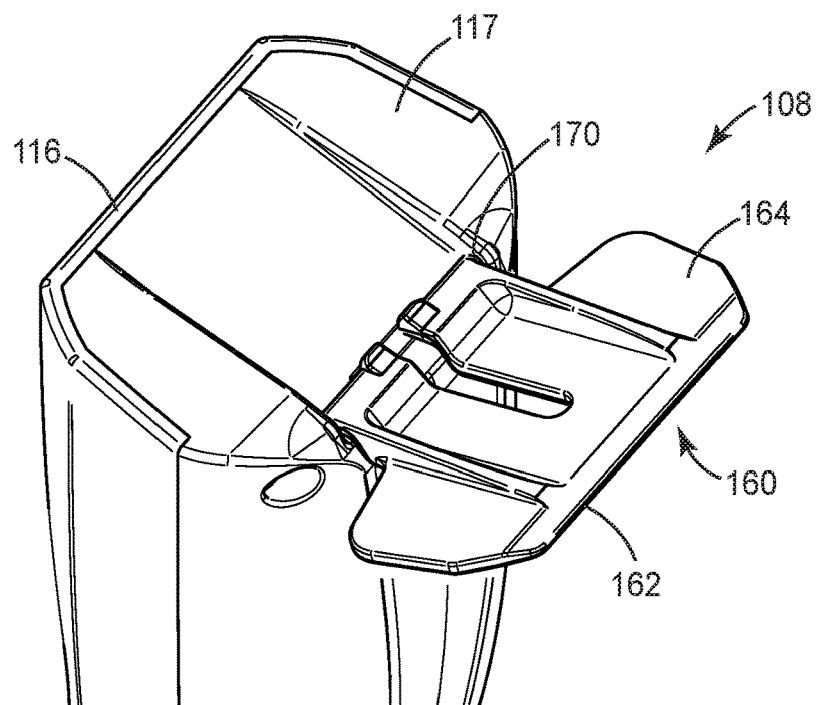
FIG. 14 is a schematic bottom perspective view of a portion of the light detection device of FIG. 10 with the support member disposed in the open position.

In one or more embodiments, the support member 160 can be adapted to selectively move from a closed position 106 to an open position 108. For example, in FIG. 13, the support member 160 is in a closed position 106, i.e., a second major surface 164 (shown in FIG. 14) faces the bottom surface 116 of the housing 112. In FIG. 14, the support member 160 is disposed in the open position 108, i.e., the second major surface 164 of the support member does not face the bottom surface 116 of the housing 112. In one or more embodiments, the support member 160 can be fixed in the open position 108 and is not movable to a closed position 106.

The support member 160 can be adapted to maintain the light detection device 110 in an upright position when the bottom surface 116 and the support member are in contact with a working surface 102 and the support member is in the open position 108 as is shown in FIG. 12. As used herein, the phrase "upright position" means that the light detection device 10 is disposed such that the top surface 114 is above the bottom surface 116 as viewed from the user's perspective, and the housing axis 104 forms an angle with a vertical axis that is less than 90°. In one or more embodiments, the housing axis 104 forms any suitable angle with the working surface 102 when the light detection device 110 is in the upright position and in contact with the working surface 102. At least a portion of the second major surface 164 of the support member 160 is adapted to contact the working surface 102 when in the open position 108 as shown in FIG.

12. Further, any suitable angle 101 can be formed between the housing axis 104 and the vertical axis 103. In one or more embodiments, angle 101 can be 0°, at least 0°, no greater than 90°, no greater than 45°, no greater than 30°, no greater than 15°.

In one or more embodiments, the bottom surface 116 can be adapted such that it is generally perpendicular to the housing axis 104. In such embodiments, the device 110 can rest on the working surface 102 such that the bottom surface 116 is flat with the working surface and the device is in a vertical position, i.e., the housing axis 104 is parallel to the vertical axis 103.

The bottom surface 116 can include a recessed portion 117 that is adapted to receive the support member 160 when the member is in the closed position 106 as is illustrated in FIG. 13. In one or more embodiments, the support member 160 is flush with the bottom surface 116 when the member is disposed within the recessed portion 117 and, therefore, in the closed position 106. In one or more embodiments, the recessed portion 117 of the bottom surface 116 of the housing 112 is adapted to engage the support member 160 in a snap-fit relationship when the support member is in the closed position 106. The support member 160 can be attached to the bottom surface 160 using any suitable hinge such that the support member can be received by a recessed portion formed in both of the front and back surfaces 113, 115.

The bottom surface 116 can also include a second recessed portion 172 that is adapted to house the hinge 170 such that the support member 160 is flush with the bottom surface 116 when in the closed position 106 (FIG. 13). The hinge 170 can be disposed in the second recessed portion 172. The second recessed portion 172 can also include a ledge 174 that is adapted to engage the support member 160 when the support member is in the open position 108 (FIG. 14). The ledge 174 can prevent the support member 160 from being over rotated such that the first major surface 162 contacts the back surface 115 of the housing 112.

The user can engage the support member 160 by engaging a portion of the member when the member is in the closed position 106, and moving the member from the closed position to the open position 108 by rotating the member about the hinge 170 until the member engages the ledge 174 of the recessed portion 172. In embodiments where the hinge 170 is a ratcheted hinge, the user can rotate the support member 160 from the closed position 106 to the open position 108 to achieve a selected angle between the first major surface 162 of the support member and the housing axis 104. Once the desired angle has been selected, the user can operate the device 110 while either holding the device in a hand or resting the device on the working surface 102 such that the device rests in an upright position at the selected angle 101 between the housing axis 104 and the vertical axis 103. If desired, the user can, in one or more embodiments, grasp the device 110 and lift it from the working surface 102 to adjust the angle between the first major surface 162 of the support member 160 and the housing axis 104, and then place the device on the working surface at a selected second angle between the housing axis 104 and the vertical axis 103.

In one or more embodiments, the support member 160 can be held in the closed position 106 using a tab or other interference feature. The support member 160 can then be released from the closed position 106 and moved to the open position 108 either manually or by using a button or switch to move the tab or interference feature out of the way. In one or more embodiments, the support member 160 can move from the closed position 106 to the open position 108 with the assistance of a spring mechanism.

Figure 16:
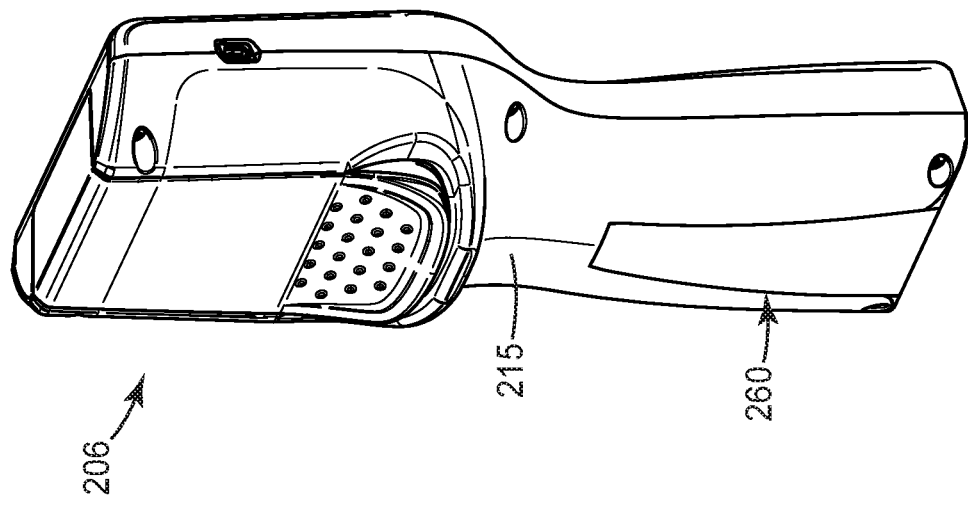
FIG. 16 is a schematic rear perspective view of the light detection device of FIG. 15 with the support member disposed in the closed position.
Figure 15:
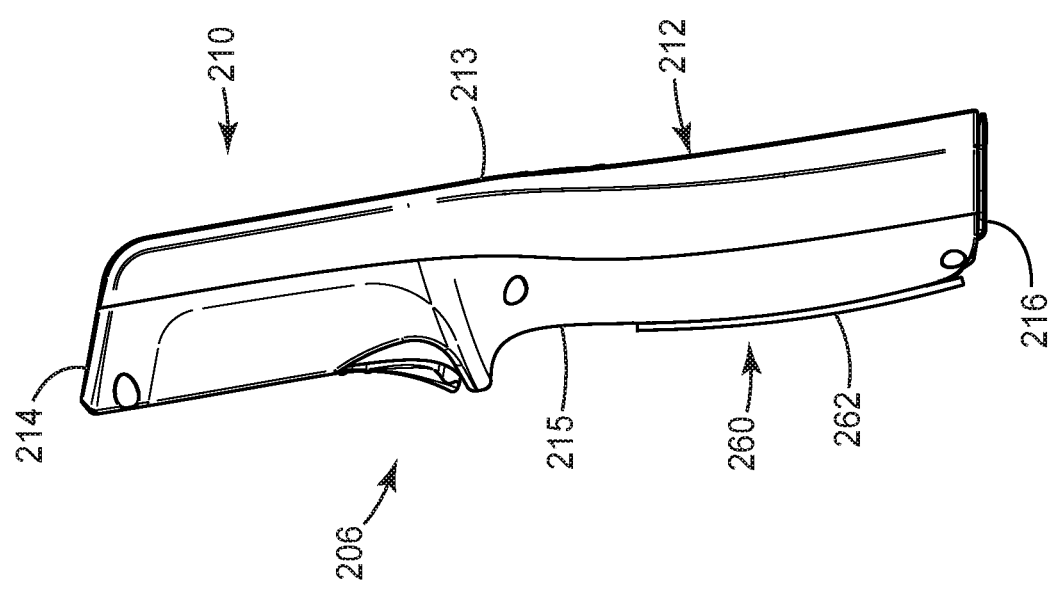
FIG. 15 is a schematic left-side view of another embodiment of a light detection device including a support member disposed in a closed position.
Figure 17:
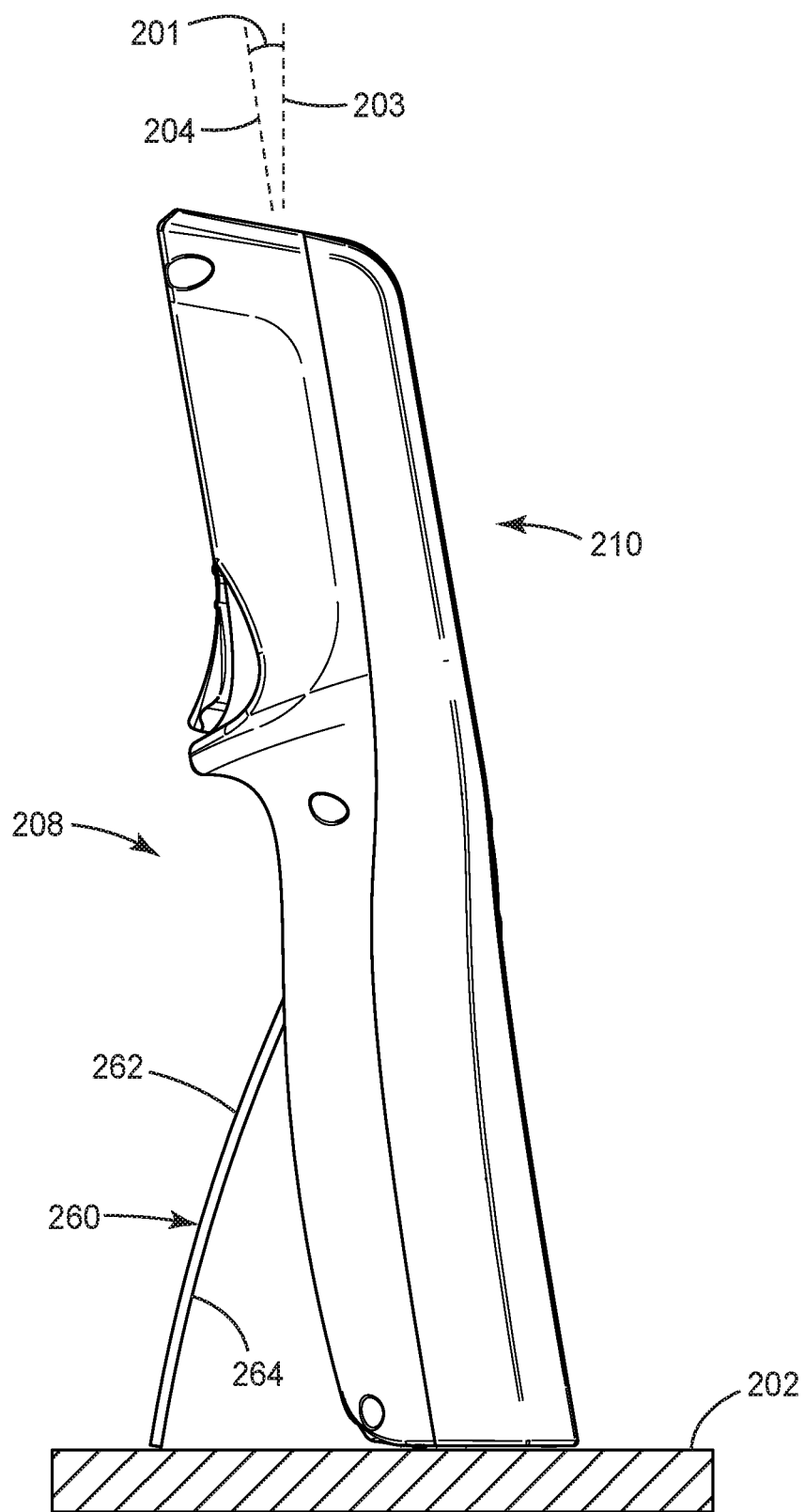
FIG. 17 is a schematic left-side view of the light detection device of FIG. 15 with the support member disposed in an open position.

As mentioned herein, the support member 160 can be connected to the housing 112 of the light detection device 110 in any suitable location. For example, FIGS. 15-17 are various views of another embodiment of a light detection device 210. All of the design considerations and possibilities regarding the light detection device 10 of FIGS. 1-9 and the light detection device 110 of FIGS. 10-14 apply equally to the light detection device 210 of FIGS. 15-17. The device 210 includes a housing 212 extending along a housing axis 204 between a top surface 214 and a bottom surface 216. The device 210 also includes a support member 260 connected to the housing 212 and adapted to be selectively moved between a closed position 206 (as shown in FIGS. 15-16) and an open position 208 (as shown in FIG. 17). The support member 260 is also adapted to maintain the light detection device 210 in an upright position when the bottom surface 216 and the support member 260 are in contact with a working surface 202 and the support member is in the open position 208 (FIG. 17). The housing axis 204 can form any suitable angle 201 with a vertical axis 203 when the bottom surface 216 and the support member 260 are in contact with the working surface 202 and the support member is in the open position 208.

One difference between device 110 of FIGS. 10-14 and device 210 of FIGS. 15-17 is that the support member 260 is attached to a back surface 215 of the housing 212 and not the bottom surface 216. In one or more embodiments, the support member 260 can be in contact with the back surface 215 of the housing when the support member is in the closed position 206 as shown in FIGS. 15-16. In the closed position 206, a first major surface 262 of the support member 260 can face away from the housing 212 and a second major surface 264 can face the housing. The back surface 215 can include a recessed portion (not shown) that is adapted to receive the support member 260 when the support member is in the closed position 206 (see FIG. 16). In one or more embodiments, the support member 260 can be snap-fit into the recessed portion such that the support member remains in the closed position 206 as the user holds the device in various orientations. For example, the support member 260 can be snap-fit within the recessed portion such that the support member remains in the closed position 206 when the device is in a horizontal orientation, i.e., the housing axis 204 is substantially parallel to a horizontal axis. In one or more embodiments, the support member 260 can be flush with the back surface 215 when the support member is in the closed position 206.

The support member 260 can be connected to the housing 212 using any suitable technique or combination of techniques. In one or more embodiments, the support member 260 can be attached to the housing with any suitable hinge. The hinge can also include a ratcheted hinge, e.g., ratcheted hinge 170 of FIGS. 13-14.

A user can grasp a portion of the support member 260 and move the support member from the closed position 206 to the open position 208 by rotating the support member about the hinge until a desired angle is formed between the first major surface 262 of the support member and the housing axis 204. The user can place the light detection unit 210 on the working surface 202 such that the support member 260 maintains the device in an upright position when the bottom surface 216 of the device and the support member are in contact with the working surface. Any suitable angle 201 can be formed between the housing axis 204 and the vertical axis 203. In one or more embodiments, the support member 260 can stabilize the light detection device 210 when the device is resting on the working surface 202.

In one or more embodiments, the support member 260 can be held in the closed position 206 using a tab or other interference feature. The support member 260 can then be released from the closed position 206 to the open position 208 either manually or by using a button or switch to move the tab or interference feature out of the way. In one or more embodiments, the support member 260 can move from the closed position 206 to the open position 208 with the assistance of a spring mechanism.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A light detection device, comprising:
    a housing comprising a top surface and a bottom surface, wherein the housing extends along a housing axis between the top surface and the bottom surface, wherein the housing further comprises a handle portion disposed between the top surface and the bottom surface;
    a port formed in the top surface of the housing, wherein the port is adapted to receive a sample; and
    a door connected to the housing, the door comprising:
        an actuator portion adapted to selectively move the door between a closed position and an open position; and
        a cover portion connected to the actuator portion and adapted to close the port when the door is in the closed position and open the port when the door is in the open position to allow external access to the port;
    wherein the light detection device is adapted to allow a user to grasp the handle portion with a hand and, with the same hand, engage the actuator portion to selectively move the door between the closed position and the open position; and
    further comprising a latch attached to the housing and adapted to hold the door in the open position, wherein the latch is further adapted to release the door when the user engages the actuator portion to move the door from the open position to the closed position;
    wherein the latch is further adapted to release the door when the user engages the actuator portion to move the door from the open position to the closed position; and wherein the light detection device is a luminometer, photometer, turbidimeter, colorimeter, or fluorometer.

2. The light detection device of claim 1, wherein the door is connected to the housing by a hinge, wherein the actuator portion is adapted to selectively move the door by rotating the door between the closed position and the open position.

3. The light detection device of claim 1, wherein the door is biased in the closed position.

4. The light detection device of claim 1, further comprising a spring disposed between the door and the housing that is adapted to bias the door in the closed position.

5. The light detection device of claim 2, further comprising a spring disposed between the door and the housing that is adapted to bias the door in the closed position.

6. The light detection device of claim 1, wherein the housing further comprises a ledge that surrounds at least a portion of the port, wherein the cover portion of the door is adapted to engage the ledge when the door is in the closed position; and wherein the housing further comprises a gasket disposed along at least a portion of the ledge, wherein the gasket is adapted to prevent moisture and ambient light from entering the port.

7. The light detection device of claim 4, wherein the door is connected to the housing by a hinge, wherein the actuator portion is adapted to selectively move the door by rotating the door between the closed position and the open position.

8. A light detection device, comprising:
    a housing comprising a top surface and a bottom surface, wherein the housing extends along a housing axis between the top surface and the bottom surface, wherein the housing further comprises a handle portion disposed between the top surface and the bottom surface;
    a port formed in the top surface of the housing, wherein the port is adapted to receive a sample; and
    a door connected to the housing, the door comprising:
        an actuator portion adapted to selectively move the door between a closed position and an open position; and
        a cover portion connected to the actuator portion and adapted to close the port when the door is in the closed position and open the port when the door is in the open position to allow external access to the port;
    wherein the light detection device is adapted to allow a user to grasp the handle portion with a hand and, with the same hand, engage the actuator portion to selectively move the door between the closed position and the open position;
    wherein the housing further comprises a ledge that surrounds at least a portion of the port, wherein the cover portion of the door is adapted to engage the ledge when the door is in the closed position; and wherein the housing further comprises a gasket disposed along at least a portion of the ledge, wherein the gasket is adapted to prevent moisture and ambient light from entering the port; and wherein the light detection device is a luminometer, photometer, turbidimeter, colorimeter, or fluorometer.

9. The light detection device of claim 8, wherein the door is connected to the housing by a hinge, wherein the actuator portion is adapted to selectively move the door by rotating the door between the closed position and the open position.

10. The light detection device of claim 8, wherein the door is biased in the closed position.

11. The light detection device of claim 8, further comprising a spring disposed between the door and the housing that is adapted to bias the door in the closed position.

12. The light detection device of claim 9, further comprising a spring disposed between the door and the housing that is adapted to bias the door in the closed position.

13. The light detection device of claim 8, further comprising a latch attached to the housing and adapted to hold the door in the open position, wherein the latch is further adapted to release the door when the user engages the actuator portion to move the door from the open position to the closed position.

14. A method, comprising:

grasping a handle portion of a housing of a light detection device, wherein the light detection device further comprises a top surface, a bottom surface, and a port formed in the top surface, wherein the handle portion is disposed between the top surface and the bottom surface;

engaging an actuator portion of a door connected to the housing to move the door from a closed position to an open position, wherein the door further comprises a cover portion connected to the actuator portion that is adapted to close the port when the door is in the closed position and to open the port when the door is in the open position to allow external access to the port;

disposing a sample within the housing through the port; and engaging the actuator portion of the door to move the door from the open position to the closed position;

and wherein the method further comprises pressing the actuator portion with a finger or thumb of a hand that is grasping the handle portion of the housing to move the door from the closed position to the open position, or maintaining a force on the actuator portion of the door to keep the door in the open position while the sample is being disposed within the housing, or measuring a characteristic of the sample after the door has been moved from the open position to the closed position, or more than one of the foregoing; and wherein the light detection device is a luminometer, photometer, turbidimeter, colorimeter, or fluorometer.

15. The method of claim 14, comprising pressing the actuator portion with a finger or thumb of a hand that is grasping the handle portion of the housing to move the door from the closed position to the open position.

16. The method of claim 14, the method comprising maintaining a force on the actuator portion of the door to keep the door in the open position while the sample is being disposed within the housing.

17. The method of claim 14, wherein engaging the actuator portion of the door to move the door from the open position to the closed position comprises releasing the actuator portion of the door to move the door from the open position to the closed position.

18. The method of claim 14, wherein the door is connected to the housing by a hinge, wherein the actuator portion is adapted to selectively move the door by rotating the door between the closed position and the open position.

19. The method of claim 14, further comprising measuring a characteristic of the sample after the door has been moved from the open position to the closed position.

* * * * *